(12) United States Patent
Giuliani et al.

(10) Patent No.: US 9,289,405 B2
(45) Date of Patent: *Mar. 22, 2016

(54) COMPOUNDS PROVIDED WITH ANTIOXIDANT ACTIVITY AGAINST FREE RADICALS, AND PHARMACEUTICAL AND COSMETIC COMPOSITIONS CONTAINING THEM

(75) Inventors: Giammaria Giuliani, Milan (IT); Anna Benedusi, Milan (IT)

(73) Assignee: GIULIANI S.P.A, Milan (IT)

( * ) Notice: Subject to any disclaimer, the term of this patent is extended or adjusted under 35 U.S.C. 154(b) by 194 days.

This patent is subject to a terminal disclaimer.

(21) Appl. No.: 13/642,853

(22) PCT Filed: Apr. 22, 2011

(86) PCT No.: PCT/IB2011/051767
§ 371 (c)(1),
(2), (4) Date: Oct. 22, 2012

(87) PCT Pub. No.: WO2011/132177
PCT Pub. Date: Oct. 27, 2011

(65) Prior Publication Data
US 2013/0046017 A1    Feb. 21, 2013

(30) Foreign Application Priority Data

Apr. 22, 2010   (IT) .............. MI2010A0691

(51) Int. Cl.
| | | |
|---|---|---|
| *A61K 31/23* | (2006.01) | |
| *A61K 31/19* | (2006.01) | |
| *A61K 31/22* | (2006.01) | |
| *A61K 45/06* | (2006.01) | |
| *A61K 8/36* | (2006.01) | |
| *A61Q 5/00* | (2006.01) | |
| *A61Q 19/00* | (2006.01) | |
| *A61Q 5/02* | (2006.01) | |

(52) U.S. Cl.
CPC ............. *A61K 31/19* (2013.01); *A61K 8/361* (2013.01); *A61K 31/22* (2013.01); *A61K 45/06* (2013.01); *A61Q 5/00* (2013.01); *A61Q 19/00* (2013.01); *A61K 2800/522* (2013.01); *A61Q 5/02* (2013.01)

(58) Field of Classification Search
None
See application file for complete search history.

(56) References Cited

U.S. PATENT DOCUMENTS

2005/0175555 A1    8/2005   Stradi et al.

FOREIGN PATENT DOCUMENTS

WO    WO 2010/052329    *    5/2010    ........... A61K 31/045

OTHER PUBLICATIONS

International Search Report and Written Opinion in connection with International Application No. PCT/IB2011/051767, mailed Jul. 19, 2011.

Mukherjee, S. et al, 2009, "Cardioprotection with the Parrodiene 2,4,6—Octatrienal and Its Potassium Salt through Activation of the Akt—Bcl-2 Survival Pathway," Journal of Natural Products, 72(5):871-875.

* cited by examiner

*Primary Examiner* — Craig Ricci
(74) *Attorney, Agent, or Firm* — DLA Piper LLP (US)

(57) ABSTRACT

The invention relates to the use of compounds of general formula (I):

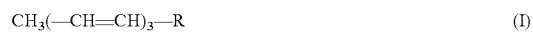

$$CH_3\text{—}(CH\text{=}CH)_3\text{—}R \qquad (I)$$

wherein R is selected from CO—O—R' or CO—O$^{(-)}$, R' being selected from H, alkyl or alkenyl from $C_1$ to $C_{22}$, or sugars, and their pharmaceutically acceptable salts, preferably such as sodium, potassium, or lysine salts,
each compound of general formula (I) being used as such or mixed with one or more of the others,
as active ingredients in a pharmaceutical or cosmetic composition provided with antioxidant activity against free radicals.

11 Claims, 1 Drawing Sheet

COMPOUNDS PROVIDED WITH ANTIOXIDANT ACTIVITY AGAINST FREE RADICALS, AND PHARMACEUTICAL AND COSMETIC COMPOSITIONS CONTAINING THEM

CROSS REFERENCE TO RELATED APPLICATIONS

This is a U.S. national stage entry of International Application No. PCT/IB2011/051767, filed on Apr. 22, 2011, which in turn claims priority to Italian Patent Application No. MI2010A000691, filed on Apr. 22, 2010, each of which is hereby incorporated by reference herein in its entirety.

FIELD OF THE INVENTION

The present invention relates to compounds provided with antioxidant activity against free radicals, for use as active ingredients for preparation of pharmaceutical or cosmetic compositions.

PRIOR ART

Antioxidant activity against free radicals has been and is the object of numerous studies both in the pharmaceutical field and in the cosmetic field. For example, EP1328268 B1 of the same applicant relates to a composition provided with said kind of activity produced by certain flavonoids extracted from red wine, in particular a combination of quercetin and catechin active ingredients formulated for oral use, which can be used in various applications in the pharmaceutical or nutritional or cosmetic field essentially based on said antioxidant activity against free radicals.

DESCRIPTION OF THE INVENTION

According to the present invention, it has now been found, surprisingly, that a remarkable antioxidant activity against free radicals is generated by compounds of general formula (I):

$$CH_3(-CH=CH)_3-R \quad (I)$$

wherein R is selected from CO—O—R' or CO—O$^{(-)}$, R' being selected from H, alkyl or alkenyl from $C_1$ to $C_{22}$, or sugars, and their pharmaceutically acceptable salts, preferably such as sodium, potassium, or lysine salts.

An experimental study, reported hereunder in the present description, in fact showed that surprisingly for said compounds of the invention it is possible to obtain significant antioxidant activity against free radicals.

The invention also relates to pharmaceutical and cosmetic compositions derived therefrom, each compound of general formula (I) being used in said compositions as such or mixed with the others.

The invention therefore relates to the use of the compounds of formula (I) as active ingredients for any therapeutic or cosmetic application in which said antioxidant activity against free radicals produces an advantageous effect. In particular this relates to applications on the human skin and scalp to combat the oxidant action of free radicals and preserve the physiological conditions of the epidermis and of the hair subjected to said action.

Characterizing data and formulae of some of the preferred compounds of general formula (I) are given below, with reference to octatrienoic acid and its salts or esters:

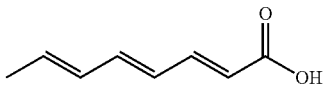

$C_8H_{10}O_2$ MW 138.17
2E,4E,6E-Octa-2,4,6-trienoic acid
CAS #: 5205-32-3

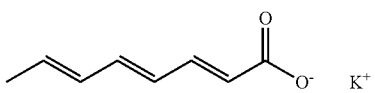

$C_8H_9O_2.K$ MW 176.26
2E,4E,6E-Octa-2,4,6-trienoic acid potassium salt
CAS #: 1147842-10-1

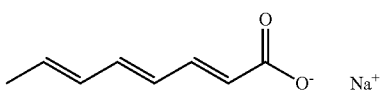

$C_8H_9O_2.Na$ MW 160.15
2E,4E,6E-Octa-2,4,6-trienoic acid sodium salt
CAS #: not available

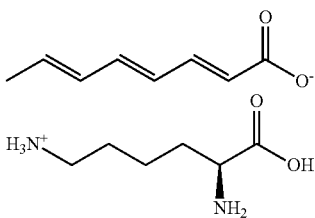

$C_8H_9O_2.C_6H_{15}N_2O_2$ MW 284.36
2E,4E,6E-Octa-2,4,6-trienoic acid L-lysine salt
CAS #: not available

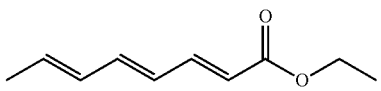

$C_{10}H_{14}O_2$ MW 166.22
2E,4E,6E-Octa-2,4,6-trienoic acid ethyl ester
CAS #5941-49-1

A composition of the invention is preferably formulated for topical administration on the skin or on the scalp, and comprises said active ingredient in a quantity ranging from 0.0003 to 0.0036 mol/100 g.

This range corresponds to a range from 0.04 to 0.6 wt. % of the composition for octatrienoic acid, or for the corresponding sodium or potassium salt or for the corresponding ethyl ester, whereas it corresponds to a range from 0.11 to 1.4 wt. % of the composition in the case of the corresponding lysine salt.

Examples are given below—not intended to be in any way limiting—of compositions suitable in particular for the cosmetic use specified herein.

The quantities of the components, identified according to the INCI nomenclature, are expressed as percentages by weight varying over the stated ranges:

EXAMPLE 1

SHAMPOO

| Component (INCI name) | Quantity w/w (%) |
|---|---|
| Disodium Laureth Sulphosuccinate | 1.00-5.00 |
| Magnesium Laureth Sulphate | 5.00-9.00 |
| PEG-7 Glyceryl Cocoate | 0.50-1.00 |
| Cocamide MIPA | 0.50-2.00 |
| PEG-200 Hydrogenated Glyceryl Palmate | 0.50-2.00 |
| Polyquaternium-10 | 0.10-0.50 |
| Tetrasodium EDTA | 0.05-0.20 |
| Sodium Lauroyl Sarcosinate | 1.00-4.00 |
| Tetrasodium EDTA | 0.05-0.20 |
| Sodium octatrienoate | 0.048-0.6 |
| BHA | 0.005-0.015 |
| Potassium Undecylenoyl Wheat Protein | 0.50-1.00 |
| Phenyl Trimethicone | 0.5-1.50 |
| Silicone Quaternium-15 | 0.01-0.07 |
| Laureth-4 | 0.01-0.80 |
| Perfume | 0.10-0.80 |
| Glycol Distearate | 0.50-1.00 |
| Laureth-7 | 0.50-0.80 |
| Sodium Cocoamphoacetate | 0.05-3.00 |
| Cocamidopropyl Betaine | 0.01-2.00 |
| Sodium Laureth Sulphate | 0.01-3.00 |
| Sodium Hydroxymethylglycinate | 0.20-0.45 |
| Benzoic acid | 0.005-0.10 |
| Citric acid | q.s. |
| Aqua | q.s. 100.00 |

EXAMPLE 2

MEDIUM-PROTECTION SUN PROTECTION

| Component (INCI name) | Quantity w/w (%) |
|---|---|
| Aqua | 40.00-60.00 |
| C12-15 alkyl benzoate | 5.00-7.00 |
| Ethylhexyl methoxycinnamate | 3.00-7.00 |
| Isostearyl isostearate | 2.00-8.00 |
| Styrene/Acrylates Copolymer | 1.00-5.00 |
| Acrylates/C10-30 Alkyl Acrylate Crosspolymer | 0.05-0.70 |
| Butylene glycol cocoate | 1.00-5.00 |
| Butyl methoxydibenzoylmethane | 1.00-5.00 |
| Diethylamino Hydroxybenzoyl Hexyl Benzoate | 1.00-5.00 |
| Ethylhexyl Triazone | 1.00-5.00 |
| Octocrylene | 1.00-5.00 |
| Polyurethane - 34 | 1.00-5.00 |
| PPG-15 stearyl ether | 1.00-5.00 |
| Diethylhexyl syringylidene malonate | 0.10-1.00 |
| Sorbityl furfural | 0.05-0.10 |
| Octatrienoic acid | 0.04-0.5 |
| Quercetin | 0.001-0.005 |
| Ethylhexylglycerin | 0.15-0.60 |
| *Coleus forskohlii* root extract | 0.005-0.50 |
| Polyperfluoroethoxymethoxy Difluoroethyl PEG Phosphate | 0.2-1.50 |
| Perfume | 0.1-0.5 |
| Phenoxyethanol | 0.80-1.00 |
| Sodium Hydroxide | q.s. |

EXAMPLE 3

LOTION AGAINST HAIR LOSS

| Component (INCI name) | Quantity w/w (%) |
|---|---|
| Alcohol denat. | 10.00-30.00 |
| Disodium EDTA | 0.025-0.20 |
| Octatrienoic acid | 0.04-0.5 |
| Biotin | 0.001-0.005 |
| Perfume | 0.30 |
| *Ajuga reptans* leaf extract | 0.01-0.05 |
| Calcium pantothenate | 0.05-0.40 |
| PEG-40 Hydrogenated Castor Oil | 0.20-1.00 |
| Aqua | q.s. 100.00 |

EXAMPLE 4

AFTER-SUN BODY MILK

| Component (INCI name) | Quantity w/w (%) |
|---|---|
| Glycerin | 1.00-6.00 |
| Methylpropanediol | 1.00-6.00 |
| Cetyl hydroxyethylcellulose | 0.10-0.40 |
| Xanthan gum | 0.10-0.40 |
| Tapioca starch | 1.00-2.00 |
| Disodium EDTA | 0.025-0.20 |
| Octatrienoic acid | 0.04-0.5 |
| Sorbitan stearate | 2.00-5.00 |
| Sucrose cocoate | 0.10-1.00 |
| Ethylhexyl palmitate | 1.00-5.00 |
| Hydrogenated polydecene | 100-5.00 |
| Caprylic/capric triglycerides | 1.00-5.00 |
| *Butyrospermum parkii* | 1.00-5.00 |
| Meadowfoam (*Limnanthes alba*) seed oil | 1.00-3.00 |
| Dimethicone | 1.00-3.00 |
| Sodium hydroxymethylglycinate | 0-10-0.20 |
| Phenoxyethanol | 0.70-0.90 |
| Lactic acid | q.s. |
| Perfume | 0.30 |
| Delta tocopherol | 0.02-0.25 |
| Sorbityl furfural | 0.10-0.90 |
| Aqua | q.s. 100.00 |

EXAMPLE 5

FACE CREAM

| Component (INCI name) | Quantity w/w (%) |
|---|---|
| Glycerin | 2.00-5.00 |
| Diglycerin | 0.20-2.00 |
| Cetearyl alcohol | 0.20-2.50 |
| Cetearyl glucoside | 0.20-2.50 |
| PEG-100 Stearate | 0.20-1.00 |
| Sorbityl furfural | 0.5-1.00 |
| Tetrasodium Glutamate Diacetate | 0.10-0.50 |
| Octatrienoic acid | 0.04-0.5 |
| Palm butter | 0.50-3.00 |
| Hydrogenated Evening Primrose Oil | 0.50-3.00 |
| Octyldodecanol | 0.50-3.00 |
| Hydrogenated castor oil | 1.00-4.00 |
| Ethylhexyl cocoate | 1.00-4.00 |
| Acrylates/C10-30 Alkyl acrylate crosspolymer | 1.00-2.00 |
| *Butyrospermum parkii* | 1.00-5.00 |
| Beta sitosterol | 0.10-0.50 |
| Delta tocopherol | 0.05-0.20 |
| Dimethicone | 0.50-1.50 |

-continued

FACE CREAM

| Component (INCI name) | Quantity w/w (%) |
|---|---|
| Dimethicone crosspolymer | 0.10-1.50 |
| Ethylhexylglycerin | 0.25-0.50 |
| Phenoxyethanol | 0.50-0.99 |
| Perfume | q.s. |
| Aqua | q.s. 100.00 |

EXAMPLE 6

LEAVE-ON MAKE-UP REMOVER

| Component (INCI name) | Quantity w/w (%) |
|---|---|
| Glycerin | 2.00-5.00 |
| Ethylhexylglycerin | 0.25-0.50 |
| Potassium octatrienoate | 0.05-0.6 |
| Trehalose | 0.50-1.00 |
| PPG-26 Buteth-26 | 2.00-15.00 |
| PEG-40 Hydrogenated Castor Oil | 2.00-15.00 |
| Methylpropanediol | 1.00-6.00 |
| Aqua | 60.00-80.00 |

Experimental Study: In-Vitro Evaluation of the Antioxidant Effects of the Compounds of the Invention The purpose of the study was to evaluate in vitro the modulation of the production of ROS (reactive oxygen species), according to FIG. 1, and lipid lipoperoxidation, according to FIG. 2, by the following compounds of the invention:
compound 1: 2E,4E,6E-octatrienoic acid
compound 2: potassium 2E,4E,6E-octatrienoate
compound 3: 2E,4E,6E-octatrienoic acid, L-lysine salt, compared with a control.

Experimental Models

Two cellular systems were used: NCTC 2544, a line of human keratinocytes, and THP-1, a human promyelocytic line. The results were expressed as mean±standard deviation. Each experiment was repeated at least twice.

Parameters Evaluated and Results Obtained a) Modulation of the Production of ROS Tributyltin (TBT) and lipopolysaccharide (LPS) are used as endogenous inducers of radical species. The production of ROS was evaluated by cytofluorometry techniques for the THP-1 cell line, using DCFH as stain.

The optimum times and concentrations for cytofluorometric measurement of ROS were identified in preliminary experiments.

The vitamin E derivative 6-hydroxy-2,5,7,8-tetramethylchroman-2-carboxylic acid (Trolox), at a concentration of 100 μM, was used as positive control.

Figure 1:
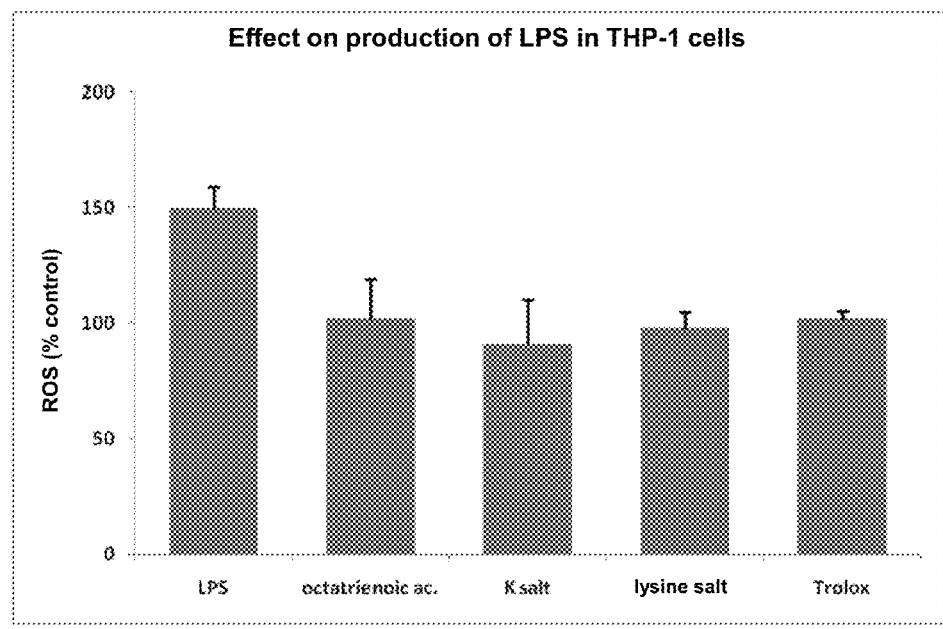
FIGS. 1 and 2 of the appended drawings show graphs taken from an experimental study as described hereunder.

The results obtained are shown in the graph in FIG. 1.

The THP-1 cells were treated for 1 hour with compounds 1 and 2 of the invention at a concentration of 100 μg/ml, with compound 3 at a concentration of 200 μg/ml and with Trolox 100 μM in serum-free medium, loaded in the last 30 minutes with DCFH (10 μM) and then treated in the presence or absence of LPS (0.1 μg/ml) and analysed in the cytofluorometer. As can be seen from the graph, the compounds of the invention proved to be capable of nullifying the production of ROS induced by LPS 0.1 μg/ml to an extent not less than Trolox.

b) Lipid Lipoperoxidation

Lipid peroxidation was evaluated on the NCTC 2544 cells by measuring the content of malondialdehyde, one of the main by-products of lipid peroxidation, through its reactivity with thiobarbituric acid. The results are expressed as absorbance/mg protein. The protein content was evaluated by the Bradford method.

The NCTC cells were treated for 24 hours in the presence or in the absence of the maximum tolerated concentration of said compounds 1, 2, 3, and then stimulated with TBT 1-2.5 μM for a further 24 hours.

Trolox 100 μM was used as positive control.

Figure 2:
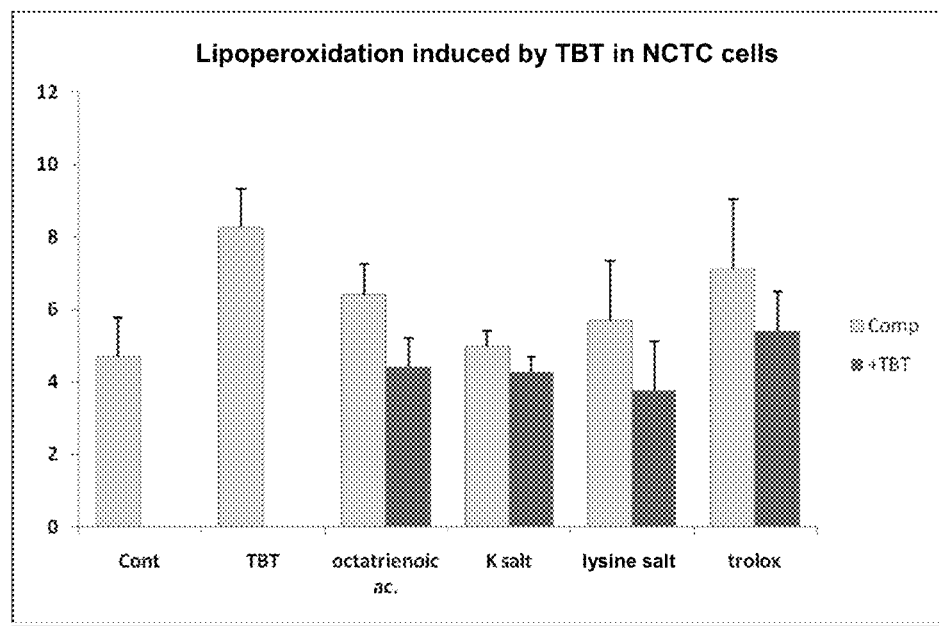

The results obtained are presented in the graph in FIG. 2.

As can be seen, for the cells treated with said compounds 1, 2, 3, a statistically significant (p<0.05) decrease of lipoperoxidation induced by TBT 2.5 μM was observed at 24 hours, confirming the effect of the invention.

The invention claimed is:

1. A method of protecting the skin and/or hair of a human subject against free radical-induced damage, comprising topically administering to the skin or scalp of a subject in need thereof an effective amount of a compound of general formula (I):

$$CH_3(-CH=CH)_3-R \quad (I)$$

wherein R is selected from CO—O—R' or CO—O$^{(-)}$; R' being selected from the group consisting of a H, an alkyl from $C_1$ to $C_{22}$, an alkenyl from $C_1$ to $C_{22}$, a sugar, and a pharmaceutically acceptable salt thereof, and each compound of general formula (I) being used as such or in a mixture with one or more of the others.

2. The method of claim 1, wherein the pharmaceutically acceptable salt is a sodium salt, a potassium salt or a lysine salt.

3. The method according to claim 1, wherein said active ingredient is 2,4,6-octatrienoic acid.

4. The method according to claim 1, wherein said active ingredient is a salt of 2,4,6-octatrienoic acid.

5. The method according to claim 4, wherein said active ingredient is the sodium salt of 2,4,6-octatrienoic acid.

6. The method according to claim 4, wherein said active ingredient is the potassium salt of 2,4,6-octatrienoic acid.

7. The method according to claim 4, wherein said active ingredient is the L-lysine salt of 2,4,6-octatrienoic acid.

8. The method according to claim 1, wherein said active ingredient is the ethyl ester of 2,4,6-octatrienoic acid.

9. The method according to claim 1, wherein said active ingredient is a mixture of two or more of the compounds of formula (I).

10. The method according to claim 1, wherein said active ingredient is formulated in a composition in a quantity ranging from 0.0003 to 0.0036 mol/100 g.

11. The method according to claim 1, wherein said active ingredient is formulated with suitable excipients for topical administration to the human skin or scalp.

* * * * *